(12) United States Patent
Nord et al.

(10) Patent No.: US 10,398,912 B2
(45) Date of Patent: Sep. 3, 2019

(54) METHOD AND APPARATUS PERTAINING TO CONFIGURING A RADIATION-DELIVERY TREATMENT PLAN

(75) Inventors: Janne Nord, Espoo (FI); Jarkko Peltola, Tuusula (FI); Lasse Toimela, Espoo (FI)

(73) Assignee: Varian Medical Systems International AG, Steinhausen (CH)

( * ) Notice: Subject to any disclaimer, the term of this patent is extended or adjusted under 35 U.S.C. 154(b) by 579 days.

(21) Appl. No.: 13/362,590

(22) Filed: Jan. 31, 2012

(65) Prior Publication Data

US 2013/0197294 A1 Aug. 1, 2013

(51) Int. Cl.
*A61N 5/10* (2006.01)

(52) U.S. Cl.
CPC .......... *A61N 5/1045* (2013.01); *A61N 5/103* (2013.01)

(58) Field of Classification Search
USPC .......................................................... 600/1
See application file for complete search history.

(56) References Cited

U.S. PATENT DOCUMENTS

| | | | |
|---|---|---|---|
| 7,668,292 B1 * | 2/2010 | Bose et al. .................. 378/65 |
| 7,773,723 B2 * | 8/2010 | Nord ................. A61N 5/1031 378/210 |
| 7,834,334 B2 * | 11/2010 | Grozinger et al. ........ 250/492.3 |
| 2004/0184578 A1 * | 9/2004 | Nakano ................. A61N 5/103 378/65 |
| 2008/0226030 A1 * | 9/2008 | Otto ..................... A61N 5/1031 378/65 |
| 2010/0150309 A1 * | 6/2010 | Nord et al. ..................... 378/65 |
| 2010/0183120 A1 * | 7/2010 | Nord ................... A61N 5/1049 378/65 |
| 2012/0004518 A1 * | 1/2012 | D'Souza et al. ............. 600/301 |
| 2013/0006537 A1 * | 1/2013 | Vilsmeier ........... A61N 5/1049 702/19 |
| 2013/0070898 A1 * | 3/2013 | Stahl ................... A61N 5/1037 378/65 |
| 2013/0131430 A1 * | 5/2013 | Froehlich ................ A61N 5/10 600/1 |

* cited by examiner

*Primary Examiner* — Thaddeus B Cox
(74) *Attorney, Agent, or Firm* — Fitch, Even, Tabin & Flannery LLP

(57) ABSTRACT

A radiation-delivery treatment plan includes a first value for a limit as pertains to motion compensation-based adjustment of a radiation-delivery parameter during a first portion of a radiation treatment session as well as a second value for that same limit during a second, different portion of the treatment session. By one approach, the radiation-delivery treatment plan selects between this first and second value as a function of a preselected parameter. Examples of such parameters include, but are not limited to, radiation-beam orientation parameters (such as a gantry-based parameter) and/or any of a variety of external surrogates.

8 Claims, 2 Drawing Sheets

US 10,398,912 B2

METHOD AND APPARATUS PERTAINING TO CONFIGURING A RADIATION-DELIVERY TREATMENT PLAN

TECHNICAL FIELD

This invention relates generally to radiation-treatment planning.

BACKGROUND

The use of radiation to treat medical conditions comprises a known area of prior art endeavor. For example, radiation therapy comprises an important component of many treatment plans for reducing or eliminating unwanted tumors. Unfortunately, applied radiation does not discriminate between unwanted structures and adjacent tissues, organs, or the like that are desired or even critical to continued survival of the patient. As a result, radiation is ordinarily applied in a carefully administered manner to at least attempt to restrict the radiation to a given target volume.

Many radiation-delivery treatment plans provide for exposing a treatment target (such as a tumor) to radiation from a plurality of different directions during a single treatment session. So-called arc therapy is one illustrative example in these regards. In such a case a gantry-based apparatus typically serves to move a radiation source along an arc about the patient during the treatment session.

In some cases administering the radiation also includes tracking motion as pertains to the patient. This can comprise, for example, real-time tracking of an absolute and/or relative position of the treatment target, critical organs to be protected from the radiation, a man-made marker, and so forth. Such tracking can also comprise, for example, tracking rhythmic movement such as the patient's breathing. In these cases the radiation-delivery treatment plan can facilitate automatically compensating for motion by automatically and responsively adjusting one or more radiation-delivery parameters. As one simple example, this can comprise shutting off the radiation source when the tracked movement reveals that the treatment target has moved beyond an expected target region.

Radiation-delivery treatment plans that compensate for motion typically employ a limit as pertains to a given motion compensation-based adjustment. Such limits, for example, can reflect physical limitations of the treatment apparatus and can serve to avoid having the treatment apparatus attempt a compensation adjustment that is physically difficult or even impossible. In another example, the limits reflect safety values that prevent delivering too much radiation to critical organs. Unfortunately, however, numerous variables are in play during a treatment session and such limits often represent a compromise between permitting dynamic flexibility on the one hand and achieving treatment goals on the other hand. This compromised result, in turn, may yield a less efficacious therapy than might in fact be possible.

BRIEF DESCRIPTION OF THE DRAWINGS

The above needs are at least partially met through provision of the method and apparatus pertaining to configuring a radiation-delivery treatment plan described in the following detailed description, particularly when studied in conjunction with the drawings, wherein.

Figure 1:
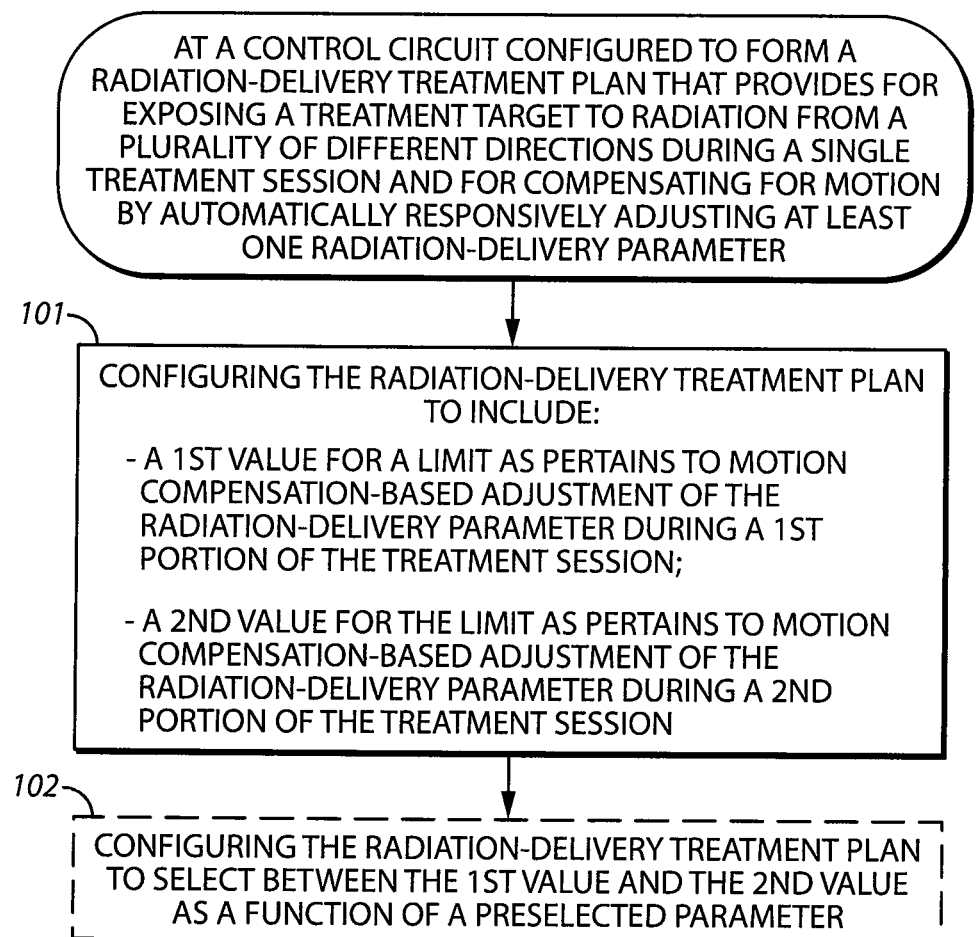
FIG. 1 comprises a flow diagram as configured in accordance with various embodiments of the invention.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, these various embodiments pertain to forming radiation-delivery treatment plans that provide for exposing a treatment target to radiation from a plurality of different directions during a single treatment session and for compensating for motion by automatically responsively adjusting at least one radiation-delivery parameter. More particularly, this disclosure provides for configuring such a radiation-delivery treatment plan to include a first value for a limit as pertains to motion compensation-based adjustment of the radiation-delivery parameter during a first portion of the treatment session as well as a second, different value for that same limit during a second, different portion of the treatment session. This approach is readily extended to any number of additional, different values for the same limit to apply to yet other portions of the treatment session.

By one approach, the radiation-delivery treatment plan selects between this first and second value as a function of a preselected parameter. Examples of such parameters include, but are not limited to, radiation-beam orientation parameters (such as a gantry-based parameter) and/or any of a variety of external surrogates.

So configured, different limit values can be applied with respect to a same radiation-delivery parameter when compensating that parameter for motion during a treatment session. This approach can help to preserve therapeutic efficacy when treating, for example, a tumor that presents different shapes and sizes when viewed from different points of reference by increasing or decreasing (as appropriate) constraints on how significant an adjustment can be made when compensating for motion when exposing the tumor to radiation from those different points of reference.

These teachings can be readily utilized in conjunction with existing radiation-delivery platforms and hence can serve to leverage the further viability and utility of those existing platforms. These teachings are also highly scalable and can be employed as subtly or as vigorously as desired and with a wide variety of treatment platforms, methodologies, radiation-delivery parameters, and modalities.

These and other benefits may become clearer upon making a thorough review and study of the following detailed description. Referring now to the drawings, and in particular to FIG. 1, an illustrative process 100 that is compatible with many of these teachings will now be presented. For the sake of clarity but without intending any particular limitations in these regards it is presumed for the sake of this description that a control circuit of choice carries out this process 100. An illustrative example in these regards appears further herein.

Generally speaking, this description also presumes that this control circuit is configured to form a radiation-delivery treatment plan that provides for exposing a treatment target to radiation from a variety of different directions during a single treatment session and to compensate for motion (that occurs during a treatment session) by automatically and responsively adjusting one or more radiation-delivery parameters. A non-exhaustive listing of such radiation-delivery parameters includes collimator position, collimator angle, collimator orientation, collimator leaf position, monitor-unit count, and patient-support position, to note but a few.

Figure 2:
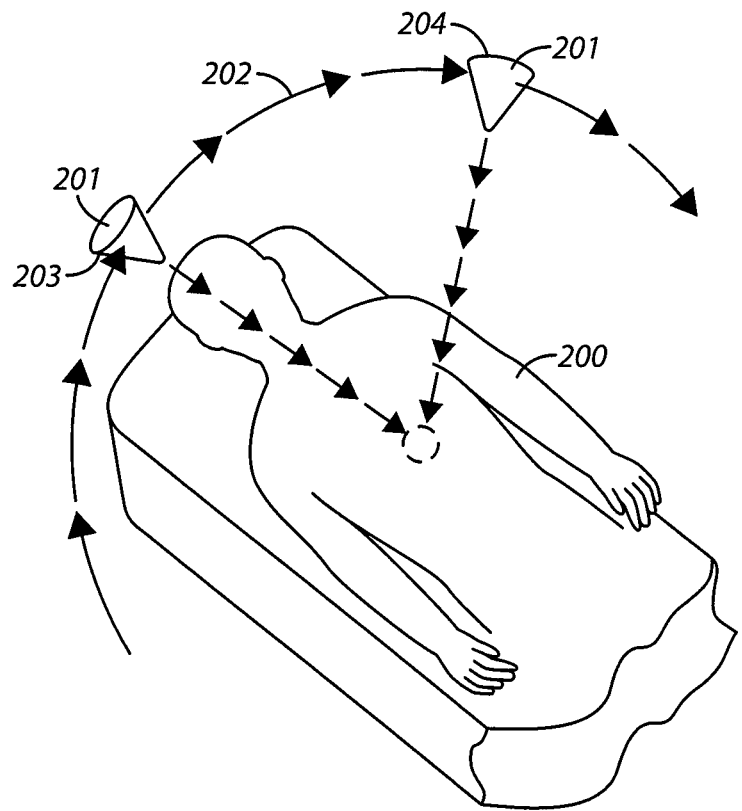
FIG. 2 comprises a perspective schematic view as configured in accordance with various embodiments of the invention.

At step 101 this process 100 provides for configuring the radiation-delivery treatment plan to include a first value for a limit at pertains to a motion compensation-based adjustment of the radiation-delivery parameter during a first portion of the treatment session. This first portion of the treatment session can comprise, for example, a respective point or location in a sequence of treatment points/locations as specified by the radiation-delivery treatment plan. FIG. 2 provides an illustrative example in this regard. In this example, a patient 200 receives radiation from a radiation source 201 that moves along an arcuate path 202 during the course of a given treatment session. Using this example, the aforementioned first portion of the treatment session could comprise the location denoted by reference numeral 203 of the radiation source 201 along that arcuate path 202.

The specific motion compensation-based adjustment will of course vary to some extent depending upon the particular radiation-delivery parameter. When the radiation-delivery parameter pertains, for example, to a physical setting for a multi-leaf collimator, the adjustment may pertain to a specific position of the collimator with respect to the radiation beam, or a particular angle (or other orientation) of that collimator with respect to the radiation beam, or a particular position for one or more of the movable leaves that comprise a multi-leaf collimator. In such cases, then, the nature of the first value for the corresponding limit can comprise, for example, a distance metric (such as a given number of millimeters, centimeters, or the like), an angular metric (such as a given number of degrees), and so forth.

Referring again to FIG. 1, step 101 also provides for configuring the radiation-delivery treatment plan to include a second value for this same limit as pertains to motion compensation-based adjustment of the radiation-delivery parameter during a second portion of the treatment session, wherein the second value is different from the first value and the second portion is different from the first portion. By way of illustration, and referring again to FIG. 2, this second position could comprise the radiation-source location denoted by reference numeral 204. As illustrated, this second position 204 is situated at a different location along the arcuate path 202 than the first position 203. As a result, these two portions have corresponding angular relationships between the radiation source 201 and the treatment target that are different from one another.

As noted above, this second value is for the same limit as the first value mentioned above. When the radiation-delivery parameter comprises, say, a collimator setting, this first value for the motion-compensation-based adjustment limit could be, say, 5 centimeters while the second value for this same limit could be, say 3 centimeters. Using this approach, the radiation-delivery treatment plan can apply different limits when effecting motion compensation at different locations of the radiation source 201 during a given treatment session. This can greatly improve the opportunity for a given radiation-delivery treatment plan to deliver, at any given moment as well as in the aggregate, an efficacious radiation dosage to the patient.

To assist in these regards, and referring again to FIG. 1, this process 100 will accommodate an optional step 102 of also configuring the radiation-delivery treatment plan to select between the aforementioned first value and second value as a function, at least in part, of a preselected parameter. As illustrated in the examples above, this preselected parameter can comprise, if desired, a radiation-beam orientation parameter such as a gantry-based parameter that corresponds to the specific location of the radiation source 201 along the aforementioned arcuate path 202.

These teachings will accommodate other approaches in these regards, however. For example, the preselected parameter could comprise, in whole or in part, an external surrogate. An external surrogate can comprise, for example, a breathing phase signal observed and calculated during the treatment session. Such an external surrogate can serve, for example, to provide information that the treatment-administration platform can use to estimate a position of, say, a critical organ that should not be irradiated and which position can inform the selection of a given limit or limits for the radiation-delivery parameter.

For the sake of simplicity and clarity, the foregoing examples makes reference to only a first and second value for only a single limit as pertains to a given corresponding radiation-delivery parameter, and only the two specifies portions of the treatment session. It will be understood, however, that this process 100 will readily accommodate an increased scaling in any of these regards. Accordingly, this process 100 can provide for supporting different values for any number of adjustments of any number of radiation-delivery parameters at any number of portions of a given treatment session. This, in turn, provides a powerful ability to optimize treatment parameters at each position of the radiation source 201 during a treatment session and thereby avoid compromises in these regards that can reduce efficacy of the treatment.

Figure 3:
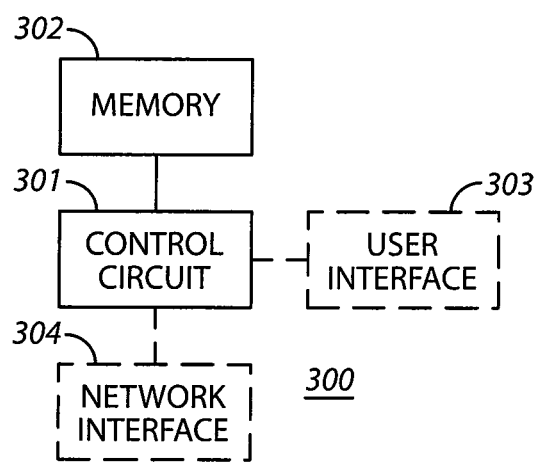
FIG. 3 comprises a block diagram as configured in accordance with various embodiments of the invention.

FIG. 3 presents an illustrative example of an apparatus 300 that accords with the present teachings. In this example the enabling apparatus 300 includes a control circuit 301 that operably couples to a memory 302 and a user interface 303. Such a control circuit 301 can comprise a fixed-purpose hard-wired platform or can comprise a partially or wholly programmable platform. These architectural options are well known and understood in the art and require no further description here. This control circuit 301 is configured (for example, by using corresponding programming as will be well understood by those skilled in the art) to carry out one or more of the steps, actions, and/or functions described herein.

The memory 302 may be integral to the control circuit 301 or can be physically discrete (in whole or in part) from the control circuit 301 as desired. This memory 302 can also be local with respect to the control circuit 301 (where, for example, both share a common circuit board, chassis, power supply, and/or housing) or can be partially or wholly remote with respect to the control circuit 301 (where, for example, the memory 302 is physically located in another facility, metropolitan area, or even country as compared to the control circuit 301).

This memory 302 can serve, for example, to non-transitorily store the computer instructions that, when executed by a computer that comprises the control circuit 301, cause the control circuit 301 to behave as described herein. (As used herein, this reference to "non-transitorily" will be understood to refer to a non-ephemeral state for the stored contents (and hence excludes when the stored contents merely constitute signals or waves) rather than volatility of the storage media itself and hence includes both non-volatile memory (such as read-only memory (ROM) as well as volatile memory (such as an erasable programmable read-only memory (EPROM).)

If desired, this apparatus 300 can also optionally include a user interface 303 and/or a network interface 304 that each operably couple to the control circuit 301. The user interface 303 can comprise one or more user-input mechanisms (such as, but not limited to, a keyboard or keypad, a cursor-control mechanism, a touch-sensitive display, a voice-recognition component, and so forth) and or user-output mechanisms (such as, but not limited to, a display, signal lights, a printer, an audio transducer, and so forth) as desired. The network interface 304 can comprise any of a variety of wireless and/or non-wireless interfaces to permit the control circuit 301 to communicate information to and/or from one or more remote resources.

Such an apparatus 300 may be comprised of a plurality of physically distinct elements as is suggested by the illustration shown in FIG. 3. It is also possible, however, to view this illustration as comprising a logical view, in which case one or more of these elements can be enabled and realized via a shared platform. It will also be understood that such a shared platform may comprise a wholly or at least partially programmable platform as are known in the art.

So configured, these teachings permit a radiation-delivery treatment plan to accommodate dynamic motion-based adjustments of one or more radiation-delivery parameters while observing different limits that are appropriate to the immediate circumstances as pertain to delivering the radiation dose. This capability, in turn, imposes fewer compromises on the planning and execution activities and permits improved delivery of radiation doses to intended targets while avoiding radiation exposure to non-targeted volumes.

Those skilled in the art will recognize that a wide variety of modifications, alterations, and combinations can be made with respect to the above described embodiments without departing from the spirit and scope of the invention, and that such modifications, alterations, and combinations are to be viewed as being within the ambit of the inventive concept.

We claim:

1. A method comprising:
at a control circuit configured to form a radiation-delivery treatment plan, wherein the radiation-delivery treatment plan provides for exposing a treatment target to radiation by a treatment apparatus from a plurality of different directions during a single treatment session and for compensating for tracked patient motion due to the patient's own movement that occurs during a radiation-delivery treatment session by automatically responsively adjusting, while exposing the treatment target to the radiation, at least one radiation-delivery parameter, provided that the radiation-delivery parameter is equal to or below a specified adjustment limit, wherein the specified adjustment limit reflects physical limitations of the treatment apparatus:
configuring the radiation-delivery treatment plan to include:
a first value for the specified adjustment limit of the radiation-delivery parameter when compensating for the tracked patient motion during a first portion of the treatment session such that the radiation-delivery parameter is prohibited from being adjusted beyond the first value for the specified adjustment limit;
a second value for the specified adjustment limit of the radiation-delivery parameter when compensating for the tracked patient motion during a second portion of the treatment session, wherein the second value is different from the first value and the second portion is different from the first portion such that the radiation-delivery parameter is prohibited from being adjusted beyond the second value for the specified adjustment limit;
and using the radiation-delivery treatment plan with a treatment apparatus comprising a radiation-delivery platform to provide radiation from a radiation source to a patient.

2. The method of claim 1 further comprising:
configuring the radiation-delivery treatment plan to select between the first value and the second value as a function of a preselected parameter.

3. The method of claim 2 wherein the preselected parameter comprises a radiation-beam orientation parameter.

4. The method of claim 3 wherein the radiation-beam orientation parameter comprises a gantry-based parameter.

5. The method of claim 2 wherein the preselected parameter comprises an external surrogate.

6. The method of claim 1 wherein the radiation-delivery parameter comprises at least one of the group consisting of:
collimator position;
collimator angle;
collimator orientation;
collimator leaf position;
monitor-unit count; and
a patient-support position.

7. The method of claim 1 wherein the first portion and the second portion comprise respective points in a sequence of treatment points that are specified by the radiation-delivery treatment plan.

8. The method of claim 1 wherein the first portion comprises when a radiation source has a first angular relationship to the treatment target and the second portion comprises when the radiation source has a second angular relationship to the treatment target, wherein the second angular relationship is different from the first angular relationship.

* * * * *